US012491338B2

(12) United States Patent
Tada et al.

(10) Patent No.: US 12,491,338 B2
(45) Date of Patent: Dec. 9, 2025

(54) CATHETER ENGAGED WITH A PUSHER

(71) Applicant: TERUMO KABUSHIKI KAISHA, Tokyo (JP)

(72) Inventors: Yuichi Tada, Santa Clara, CA (US); Yoichiro Kuwano, Tokyo (JP); John Barritt, San Jose, CA (US); Mike Foster, East Palo Alto, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 690 days.

(21) Appl. No.: 17/958,064

(22) Filed: Sep. 30, 2022

(65) Prior Publication Data

US 2024/0091500 A1 Mar. 21, 2024

Related U.S. Application Data

(60) Provisional application No. 63/407,550, filed on Sep. 16, 2022.

(51) Int. Cl.

*A61M 25/00* (2006.01)
*A61M 25/06* (2006.01)

(52) U.S. Cl.

CPC .... *A61M 25/0097* (2013.01); *A61M 25/0662* (2013.01); *A61M 2025/0681* (2013.01)

(58) Field of Classification Search

CPC ........ A61B 17/320758; A61B 17/3207; A61B 17/32037; A61B 2017/320791; A61B 2017/320766; A61B 2017/320775; A61B 2017/22071; A61B 2017/22068; A61B 2017/22045; A61B 2017/22039; A61M 2025/0681; A61M 25/0097; A61M 25/0662; A61M 25/005; A61M 25/0023

USPC .......................................................... 606/159

See application file for complete search history.

(56) References Cited

U.S. PATENT DOCUMENTS 7,981,128 B2 7/2011 To et al.
8,007,506 B2 8/2011 To et al.
8,070,762 B2 12/2011 Escudero et al.
8,236,016 B2 8/2012 To et al.
8,337,516 B2 12/2012 Escudero et al.
8,361,094 B2 1/2013 To et al.
8,628,549 B2 1/2014 To et al.
8,647,355 B2 2/2014 Escudero et al.
8,795,306 B2 8/2014 Smith et al.
8,888,801 B2 11/2014 To et al.
8,920,448 B2 12/2014 To et al.
9,095,371 B2 8/2015 Escudero et al.

(Continued)

*Primary Examiner* — Jocelin C Tanner

(74) *Attorney, Agent, or Firm* — Kim & Stewart LLP

(57) ABSTRACT

A catheter for removing an object in a body lumen includes an outer tube, a shaft surrounded by the tube, a cutting member connected to the shaft to be rotated with respect to a rotation axis, a guide wire tube attached to the outer tube and having a first lumen for a guide wire and second lumens, a metal member attached to the wire tube, a part of the metal member surrounded by the member, a distal tip attached to the wire tube and having a third lumen communicating with the first lumen, and a pusher extending along the shaft, connectable to the distal tip or the metal member, and including wires that can pass through the second lumens. The pusher causes the cutting member to move toward a first surface of the body lumen when contacting an opposite second surface of the body lumen.

21 Claims, 16 Drawing Sheets

(56) References Cited

U.S. PATENT DOCUMENTS

| | | | |
|---|---|---|---|
| 9,198,679 B2 | 12/2015 | To et al. | |
| 9,308,016 B2 | 4/2016 | Escudero et al. | |
| 9,314,263 B2 | 4/2016 | Escudero et al. | |
| 9,333,007 B2 | 5/2016 | Escudero et al. | |
| 9,345,511 B2 | 5/2016 | Smith et al. | |
| 9,492,192 B2 | 11/2016 | To et al. | |
| 9,492,193 B2 | 11/2016 | To et al. | |
| 9,668,767 B2 | 6/2017 | To et al. | |
| 9,675,376 B2 | 6/2017 | To et al. | |
| 2015/0141816 A1 | 5/2015 | Gupta et al. | |
| 2020/0093510 A1* | 3/2020 | Tada | A61B 17/320758 |

* cited by examiner

CATHETER ENGAGED WITH A PUSHER

CROSS REFERENCE TO RELATED APPLICATIONS

This patent application claims priority to U.S. Provisional Patent Application No. 63/407,550, titled "CATHETER ENGAGED WITH A PUSHER" and filed on Sep. 16, 2022. This application is herein incorporated by reference in its entirety.

TECHNICAL FIELD

Embodiments of the present disclosure relate generally to a catheter, a medical device, and a method for removing an object in a body lumen.

BACKGROUND

Medical devices that have a catheter including a rotatable drive shaft and a cutting member are widely used to remove an object from a body lumen such as a blood vessel. Such medical devices have a motor for generating torque and a hub for storing mechanism to transmit the generated torque to the cutting member through the drive shaft.

A catheter has at its distal end a guide wire lumen into which a guide wire for guiding the catheter inside a body lumen is inserted. At the beginning of an operation, an introducer sheath is inserted into the body vessel, and then the guide wire is inserted through the sheath toward and beyond a target object to be removed. Subsequently, the guide wire outside the body is inserted into the guide wire lumen of the catheter, which is then inserted into the body lumen along the guide wire. Once the distal end of the catheter has reached the object, the cutting member is rotated, and the catheter is further moved forward so that the cutting member contacts and cuts the object.

A conventional standardized catheter has a cutting diameter of up to 2 mm and thus can effectively cut an object that is present in a body lumen of up to 2 mm. However, using the conventional standardized catheter, it is difficult to effectively cut an object that is present in a body lumen of a larger diameter.

SUMMARY OF THE INVENTION

In an embodiment, a catheter for removing an object in a body lumen includes an outer tube, a rotatable drive shaft surrounded by the outer tube, a cutting member connected to a distal end of the drive shaft to be rotated by the drive shaft with respect to a rotation axis and by which the object is cut, a guide wire tube attached to a distal end of the outer tube and having a plurality of lumens extending parallel to the rotation axis, the plurality of lumens including a first lumen through which a guide wire can pass and one or more second lumens, a metal member attached to the guide wire tube, a part of the metal member being surrounded by the cutting member, a distal tip attached to a distal end of the guide wire tube and having a third lumen extending parallel to the rotation axis and communicating with the first lumen, and a pusher at least partially extending along the drive shaft, connectable to either the distal tip or the metal member, and including one or more first wires that can pass through the second lumens. The pusher causes the cutting member to move toward a first inner surface of the body lumen when the pusher contacts a second inner surface that is on an opposite side of the body lumen with respect to the first inner surface.

DESCRIPTION OF EMBODIMENTS

The following detailed description describes a catheter, a medical device, and a method for cutting an object inside a body lumen. In the present specification, a side of the medical device or the catheter which is inserted into a body lumen is defined as a distal side, and the other side of the medical device which is held by an operator during an operation is defined as a proximal side.

Figure 1:
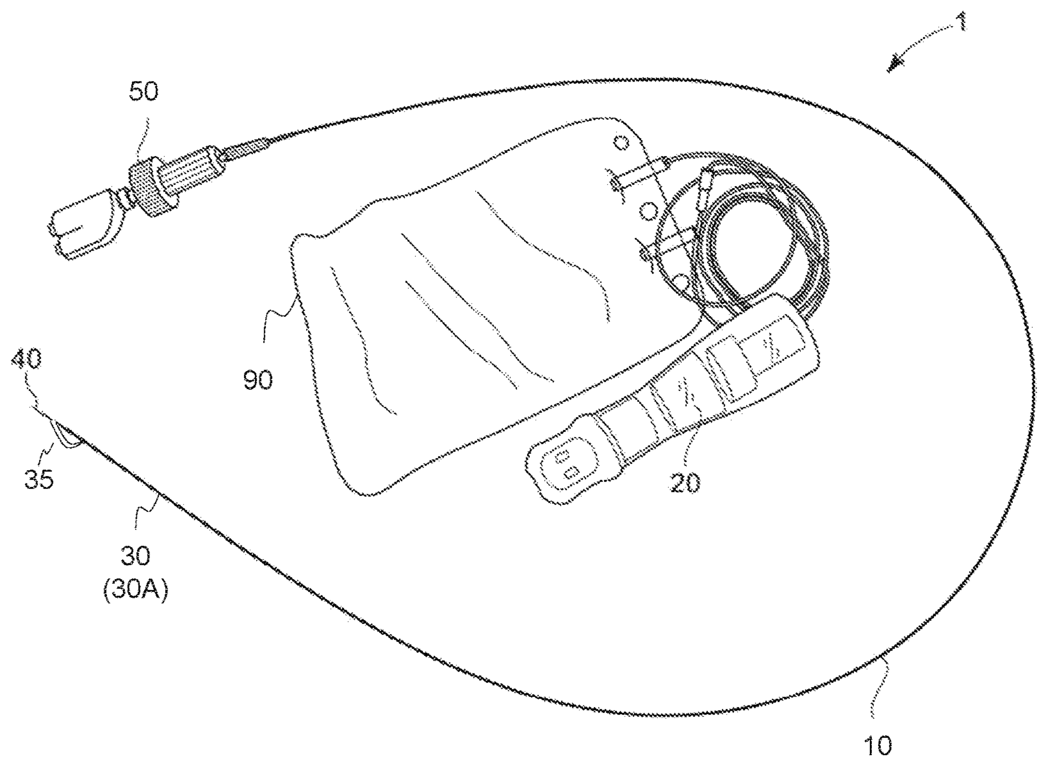
FIGS. 1-2 depict a medical device including a catheter and a handle.
Figure 2:
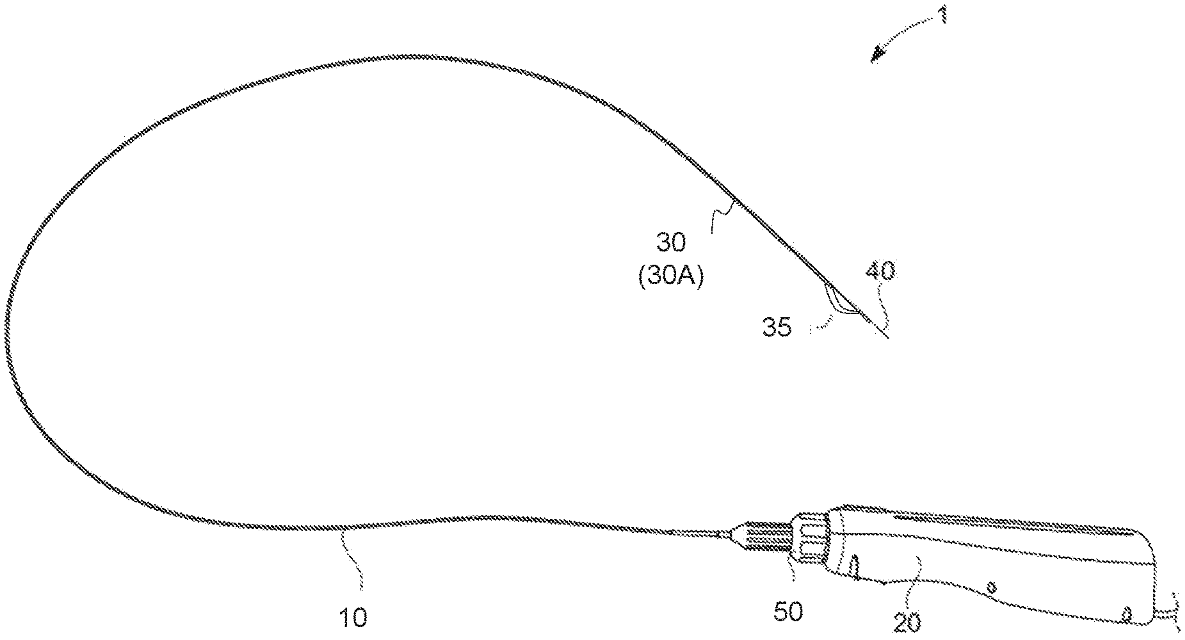

FIGS. 1-2 depict a medical device 1 in one embodiment. As shown in the figures, the medical device 1 includes a catheter 10 to be inserted into a body lumen for removing an object and a handle 20 held by an operator. The handle 20 includes a torque generating element such as a motor and an aspiration pump to aspirate the object that has been removed from the body lumen. FIG. 1 shows a state of the medical device 1 in which the catheter 10 is detached from the handle 20, and FIG. 2 shows a state in which the catheter 10 is attached to the handle 20.

The catheter 10 includes an elongated drive shaft 30 surrounded by an outer tube 30A and rotatable therein, and further includes, at its distal end, a cutting member 40 that rotates together with the drive shaft 30 to cut an object. For example, the cutting member 40 is a directional cutter for removing an object located in a particular direction. At the proximal end of the catheter 10, a hub 50 for housing rotating and aspiration mechanisms is attached. The hub 50 can be integrated into the catheter 10 or detachable from the catheter 10.

The drive shaft 30 has the characteristics of being flexible and capable of transmitting rotational power applied from the proximal side to the distal side. Specifically, the drive shaft 30 transmits the rotational torque generated by the torque generating element to the cutting member 40. The drive shaft 30 has an aspiration lumen through which the object that has been cut by the cutting member 40 is moved to the proximal side. The aspirated object is stored in a collection bag 90. The drive shaft 30 penetrates the outer tube 30A, and the cutting member 40 is fixed to the distal end of the drive shaft 30. The proximal portion of the drive shaft 30 is positioned inside of the hub 50.

The drive shaft 30 has a distal opening at which the aspiration lumen opens at the distal end thereof. The distal opening is an entrance into which the cut object enters. The proximal end of the drive shaft 30 is connected to an aspiration port through which the object that has entered the drive shaft 30 is discharged.

In one embodiment, the catheter 10 is inserted into a body lumen to be engaged with a pusher 35. The pusher 35 includes a distal portion that is bent as shown in FIGS. 1-2 and one or more elongated wires that extend away from the proximal side of the distal portion. Similar to a guide wire that is used to navigate the catheter 10 inside a body lumen, the wires (not shown in FIGS. 1-2) of the pusher 35 guide the catheter 10 to a cutting position within the body lumen. In addition, when the catheter 10 is engaged with the pusher 35, the pusher 35 introduces a bend to the distal portion of the catheter 10 to allow the catheter 10 to achieve a larger cutting diameter than the catheter 10 can achieve without the pusher 35. The detail of the structure of the pusher 35 is described later.

The handle 20 is detachable from the catheter 10 to be reusable in multiple medical procedures. When a medical procedure is performed, the handle 20 is attached to the catheter 10 via the hub 50 so that the drive shaft 30 and the cutting member 40 can rotate according to the torque generated by the torque generating element housed in the handle 20. Thereafter, the drive shaft 30 and the cutting member 40 are inserted into a body lumen, e.g., a vein, using a guide wire. In one embodiment, the hub 50 and the handle 20 may be integrated into a single component so as not to be detachable.

Further details of the aspiration and torque generating mechanisms are described in U.S. application Ser. No. 16/998,824, the entire contents of which are incorporated by reference herein.

Figure 3:
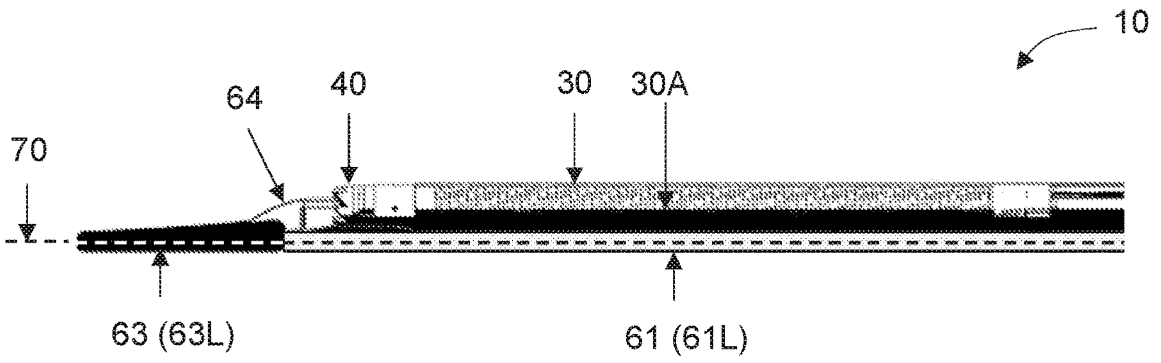
FIGS. 3-4 depict a distal portion of the catheter.
Figure 4:
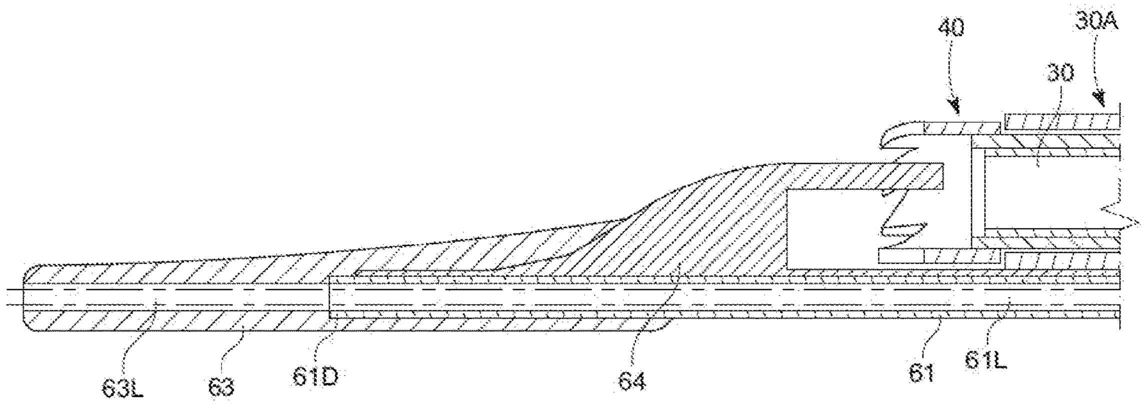

FIGS. 3-4 each show a distal portion of the catheter 10. The pusher 35 is not shown in these figures. As described above, the catheter 10 includes the cutting member 40 at the distal end thereof. The catheter 10 further includes a guide wire tube 61 having a guide wire lumen 61L, and a distal tip 63 having a guide wire lumen 63L. The distal end of the catheter 10 is inserted into a body lumen along a guide wire 70 in a state in which the guide wire 70 passes through the guide wire lumens 61L and 63L. FIG. 4 shows the guide wire lumens 61L and 63L that form a single path for the guide wire 70 to pass. For example, the proximal end 61P (see FIG. 7) of the guide wire lumen 61L is at a distance of 4 mm to 310 mm from the distal end 61D thereof. The catheter 10 and the guide wire 70 are connected to each other in a body lumen only through the guide wire lumens 61L and 63L.

For example, the guide wire tube 61 is formed of polyimides, PEEK, and the like. The guide wire tube 61 can be fixed to the outer tube 30A by, e.g., a heat-shrinkable tube (not shown) that shrinks at a temperature lower than the guide wire tube 61 so that the guide wire tube 61 is strongly fixed to the outer tube 30A when heated. Alternatively, the guide wire tube 61 can be bonded to the outer tube 30A directly. The distal tip 35 is a resin, preferably a thermoplastic resin, which is softer than the guide wire tube 61 so that the catheter 10 can proceed smoothly inside a body lumen.

The catheter 10 further includes a metal member 64 on the distal side of the cutting member 40, which stops the cutting member 40 from proceeding further when the catheter 10 is unintentionally guided toward the body lumen. The metal member 64 is formed of a metal material such as stainless steel and is fixed to the guide wire tube 61. A distal portion of the metal member 64 is attached to and covered by the distal tip 63.

Figure 5:
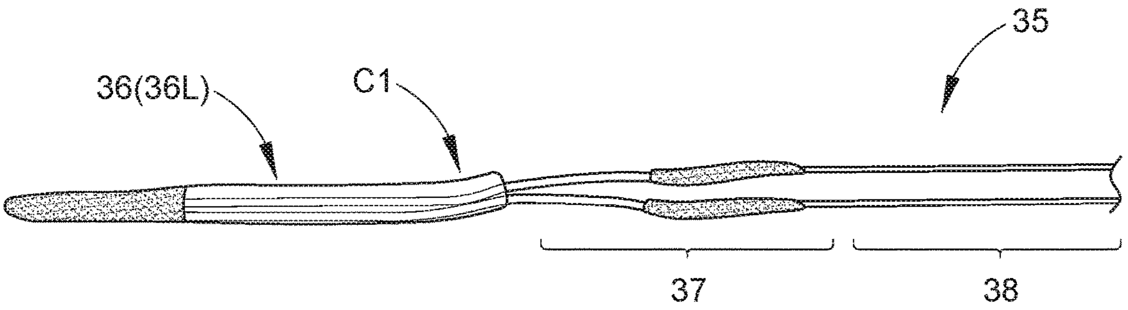
FIGS. 5-6 depict a pusher according to a first embodiment.
Figure 6:
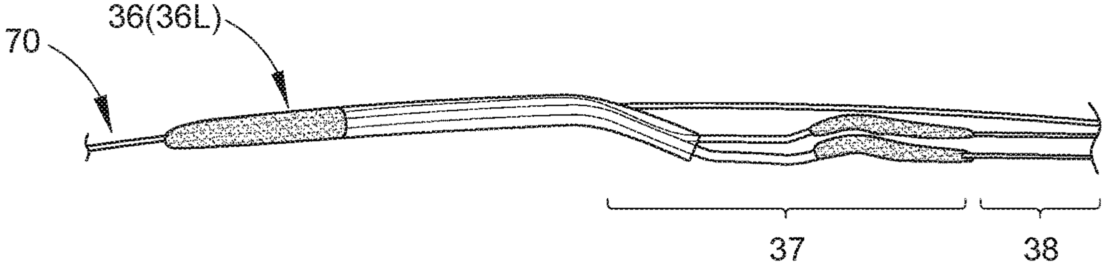

FIGS. 5-6 depict a pusher according to a first embodiment. FIG. 5 is a perspective top view of a distal portion of the pusher 35 and FIG. 6 is a perspective side view of the distal portion of the pusher 35.

The distal portion of the pusher 35 includes a head portion 36 and a bent portion 37. Also depicted in FIGS. 5-6 is the straight portion 38 of the pusher 35, which is formed of two elongated wires that extend from the proximal side of the distal portion. The head portion 36 has a guide wire lumen 36L through which the guide wire 70 can pass, which allows the pusher 35 to be navigated by the guide wire 70 inside a body lumen. The head portion 36 further includes a resin member to which the distal end of the distal tip 36 is connected at a position Cl to engage the catheter 10 with the pusher 35. The bent portion 37 includes two wires that are contiguous with, but are thicker and stiffer than, the two elongated wires of the straight portion 38, respectively.

Figure 7:
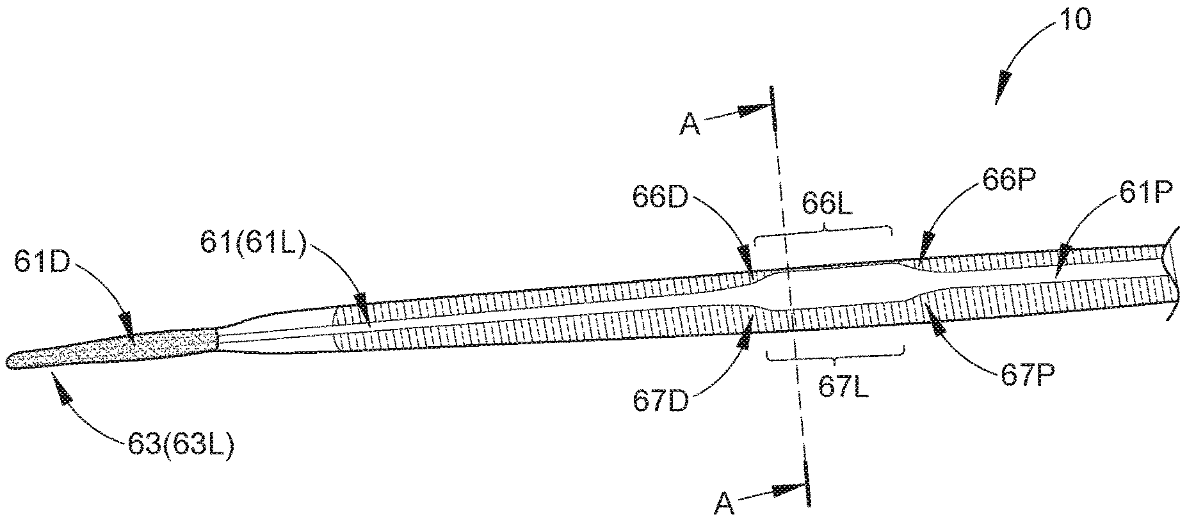
FIGS. 7-8 depict a catheter to be used with the pusher according to the first embodiment.
Figure 8:
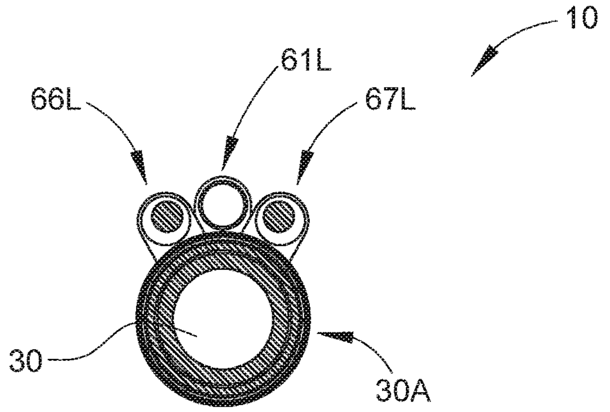

FIGS. 7-8 depict a catheter 10 to be used with the pusher 35 according to the first embodiment. The guide wire tube 61 extends along the distal portion of the outer tube 30A and includes a guide wire lumen 61L through which the guide wire 70 can pass and two additional lumens 66L and 67L through which the straight portion 38 of the pusher 35, which is formed of two elongated wires, can pass. For example, the distal ends 66D and 67D of the lumens 66L and 67L are located at a distance of 5 mm to 40 mm from the distal end of the outer tube 30A, and the length of each of the lumens 66L and 67L (i.e., the distance between 66D and 66P and 67D and 67P) is 3 mm to 300 mm.

FIG. 8 is a cross-section of the catheter 10 taken along line A-A shown in FIG. 7. In one embodiment, the guide wire lumen 61L is between the lumens 66L and 67L. The locations of the lumens 66L and 67L are not limited to the ones shown in FIG. 8. For example, the lumens 66L and 67L may be separated from the guide wire lumen 61L, and may also be formed on the opposite side of the guide wire lumen 61L with respect to the drive shaft 30. More generally, the lumens 66L and 67L can be formed at any locations along the outer tube 30A.

Figure 9:
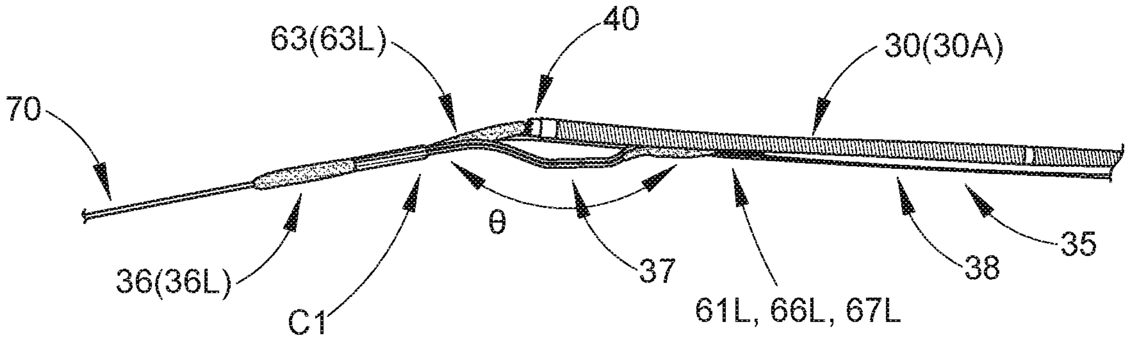
FIGS. 9-10 depict the catheter of FIGS. 7-8 connected to the pusher according to the first embodiment.
Figure 10:
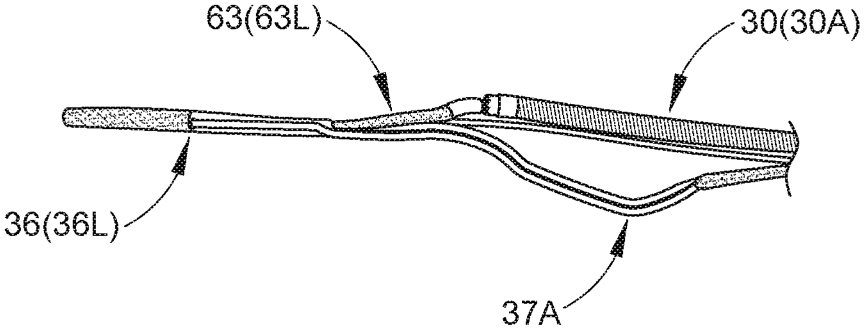

During operation, the guide wire 70 is first inserted into the body lumen. Then, the pusher 35 with the guide wire 70 inserted into the guide wire lumen 36L, is navigated to a position near the object to be cut. With the pusher 35 positioned near the object to be cut, the guide wire 70 and the wires of the straight portion 38 of the pusher 35 are inserted into the guide wire lumen 61L and the lumens 66L and 67L, respectively. Then, the catheter 10 is inserted into the body lumen until the distal end of the distal tip 63 of the catheter 10 connects to the resin member of the head portion 36 at the position Cl to engage the catheter 10 with the pusher 35 as shown in FIG. 9. When the catheter 10 is engaged with the pusher 35 in this manner, a bend is introduced in the distal portion of the catheter 10 as a result of forces applied to the catheter 10 in different directions by the guide wire 70 and the wires of the straight portion 38 of the pusher 35. The angle of the bend is depicted in FIG. 9 as 0 and this angle is dependent on the angle between the head portion 36 and the straight portion 38 of the pusher 35. The bent portion 37 may have any shape as long as the head portion 36 is at an angle with respect to the straight portion 38. Preferably, the angle θ is between 120 and 180 degrees. FIG. 10 depicts a pusher 35 having a bent portion 37A with a different shape.

Figure 11:
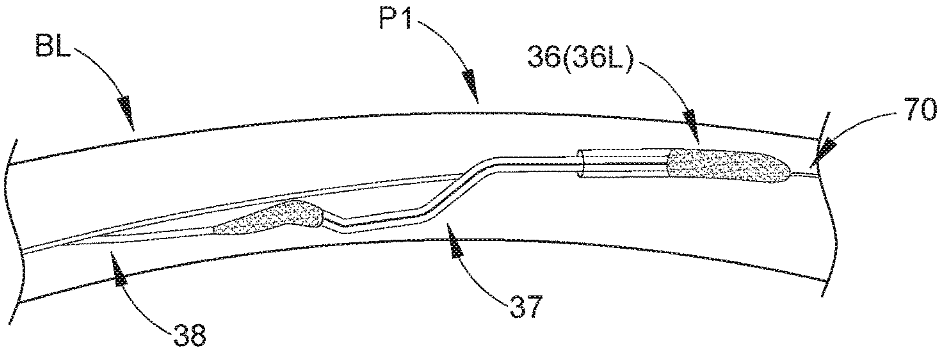
FIGS. 11-13 depict the catheter of FIGS. 7-8 connected to the pusher according to the first embodiment in a model of a body lumen.
Figure 12:
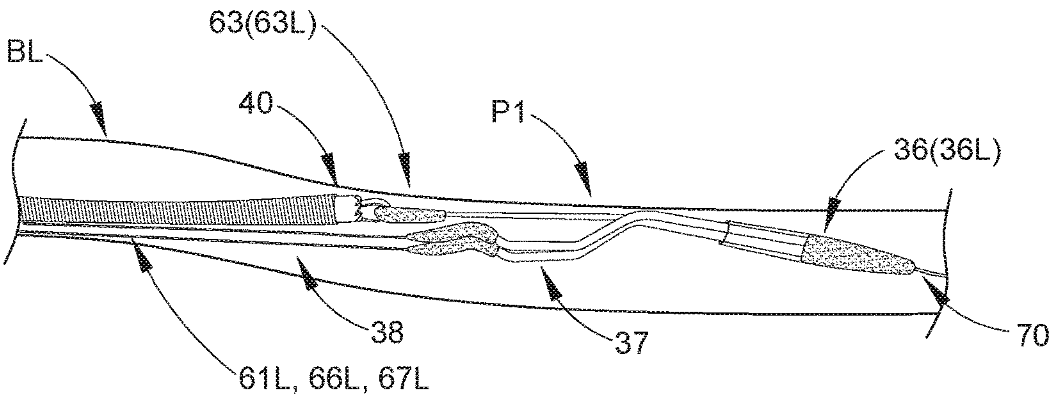
Figure 13:
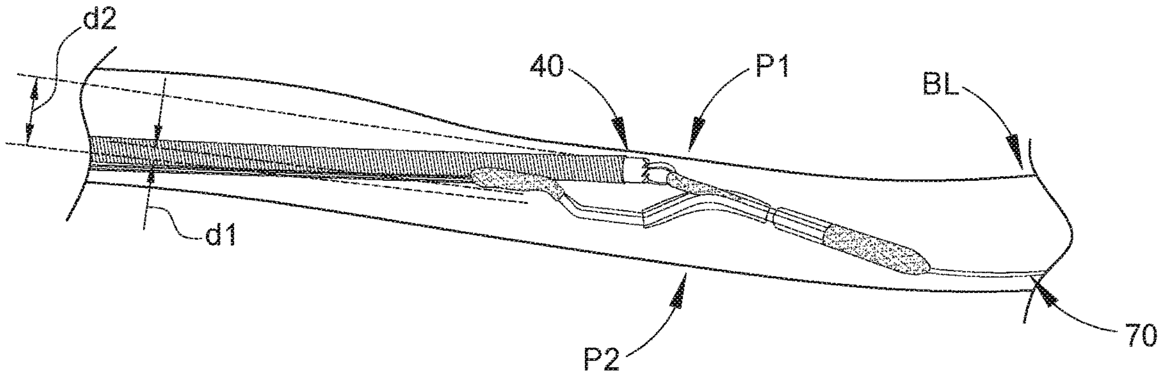

FIGS. 11-13 depict the catheter 10 guided along a guide wire 70 inside a model of a body lumen BL. As shown in FIG. 11, during operation, the guide wire 70 is inserted into the body lumen BL, and then the pusher 35 is inserted along the guide wire 70 in a state in which the guide wire 70 passes through the guide wire lumen 36L. As described above, the proximal end of the pusher 35 (i.e., the straight portion 38) is kept outside of the body lumen BL. Once the bent portion 37 of the pusher 35 has reached a cutting target position P1 where an object to be removed is located, the drive shaft 30 is inserted into the body lumen BL such that the guide wire 70 passes through the guide wire lumen 61L and the wires of the straight portion 38 pass through the lumens 66L and 67L, as shown in FIG. 12. In other words, the catheter 10 is inserted into the body lumen BL and moved forward along both the guide wire 70 and the pusher 35. After the distal tip 63 reaches and connects with the resin portion of the head portion 36 of the pusher 35, the catheter 10 is further pushed forward with the position of the pusher 35 maintained with respect to the catheter 10, resulting in bending of the drive shaft 30 as shown in FIG. 13.

In the state of the catheter 10 shown in FIG. 13, the cutting member 40 can be manipulated to the cutting target position P1 on an inner surface of the body lumen BL to remove an object located thereat. After removing the object at the cutting target position P1, the cutting member 40 can be manipulated to another cutting target position on the other side of the body lumen BL. As a result, the effective cutting radius is increased from d1 corresponding to the cutting radius that the catheter 10 would be able to achieve without the pusher 35 to d2 corresponding to the cutting radius that the catheter 10 would be able to achieve with the pusher 35.

Figure 14:
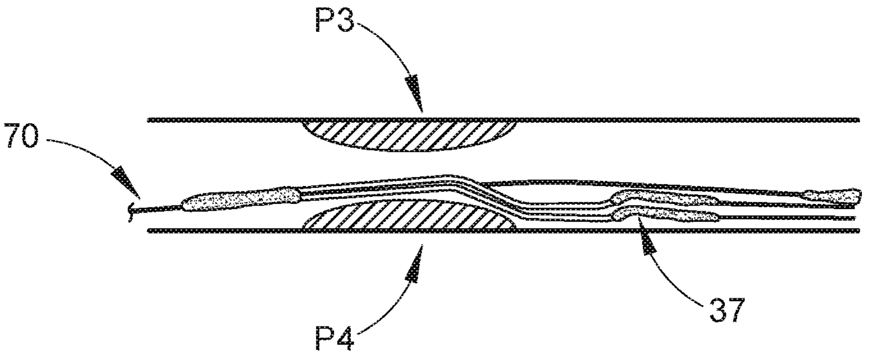
FIGS. 14-15 depict the catheter of FIGS. 7-8 approaching an object to be removed in a body lumen.
Figure 15:
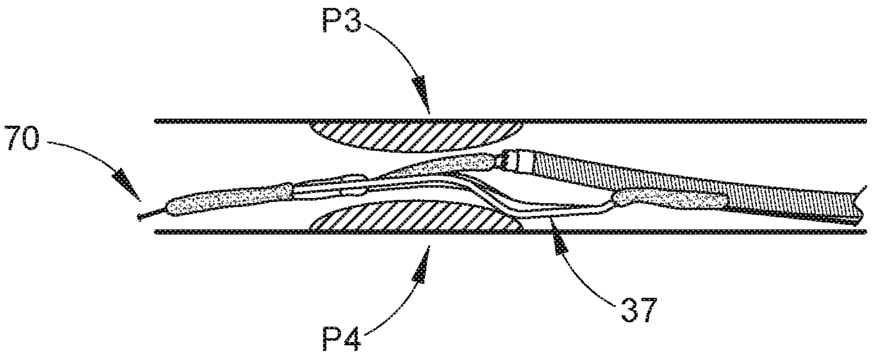

FIGS. 14-15 depict the catheter 10 of FIGS. 7-8 approaching target objects formed on a body lumen. As explained with reference to FIGS. 11-13, during operation, the guide wire 70 and the pusher 35 are inserted into a body lumen first. As shown in FIG. 14, the operator moves the pusher 35 along the guide wire 70 to reach positions P3 and P4 at which the target objects are formed. The operator then inserts the catheter 10 until the distal tip 63 reaches and is connected to the head portion 36 of the pusher 35. In that state, as shown in FIG. 15, the operator further moves the pusher 35 and the catheter 10 forward along the guide wire 70. By this operation, the cutting portion 40 is directed toward the object at position P3 because the bent portion 37 of the pusher 35 contacts the body lumen and/or the object near and at position P4, thereby pushing the catheter 10 upward. Similarly, the object on the opposite side at position P4 can be removed by changing the orientation of the catheter 10. As a result, deeper removal of an object such as a lesion formed on a body lumen is achieved.

Figure 16:
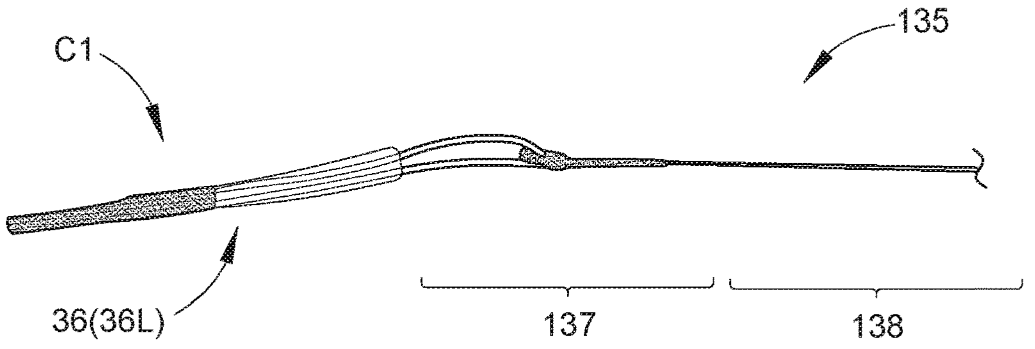
FIG. 16 depicts a pusher according to a second embodiment.

FIG. 16 depicts a pusher 135 according to a second embodiment. Unlike the pusher 35 described above, the pusher 135 has a bent portion 137 where two wires of the bent portion 137 are merged into a single wire, and the single wire extends toward the proximal side as a straight portion 138. The other elements are similar to the pusher 35, and the similar effects can be achieved.

Figure 17:
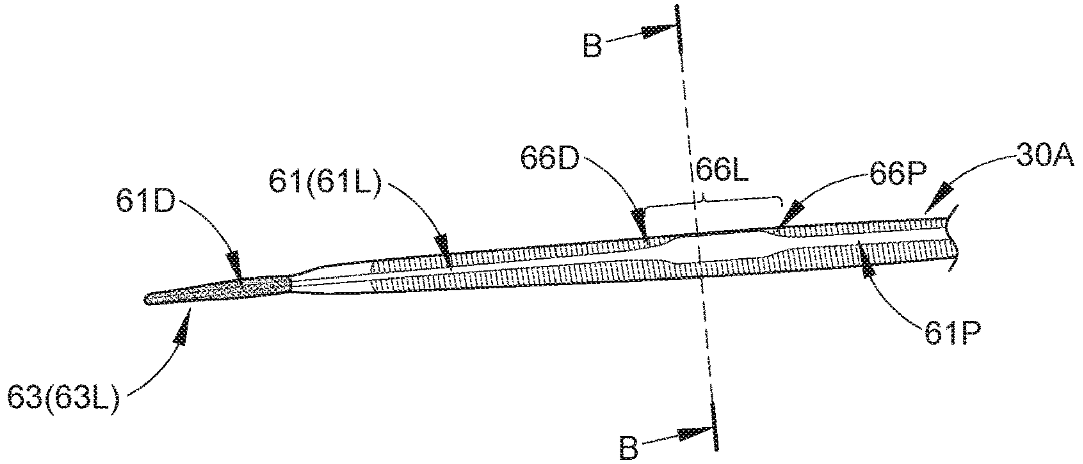
FIGS. 17-18 depict a distal portion of a catheter to be used with the pusher according to the second embodiment.
Figure 18:
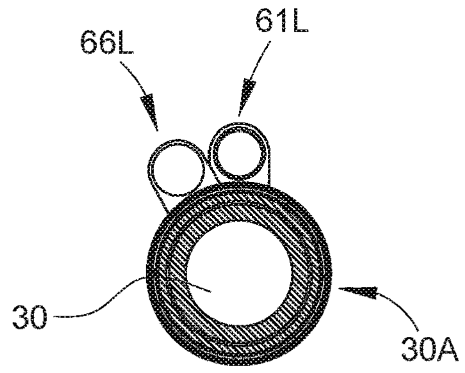

FIGS. 17-18 depict a distal portion of a catheter 10 to be used with the pusher 135 according to the second embodiment. FIG. 17 depicts a distal portion of the catheter 10 that engages with the pusher 135. Since the straight portion 138 of the pusher 135 is formed of a single wire, only a single lumen 66L is formed along the outer tube 30A. FIG. 18 is a cross-section of the catheter 10 taken along line B-B shown in FIG. 17. As depicted in FIG. 18, the guide wire lumen 61L and the lumen 66L are formed on the outer tube 30A. The lumen 66L can be formed adjacent to the guide wire lumen 61L as shown in FIG. 18 or at any location along the outer tube 30A.

Figure 19:
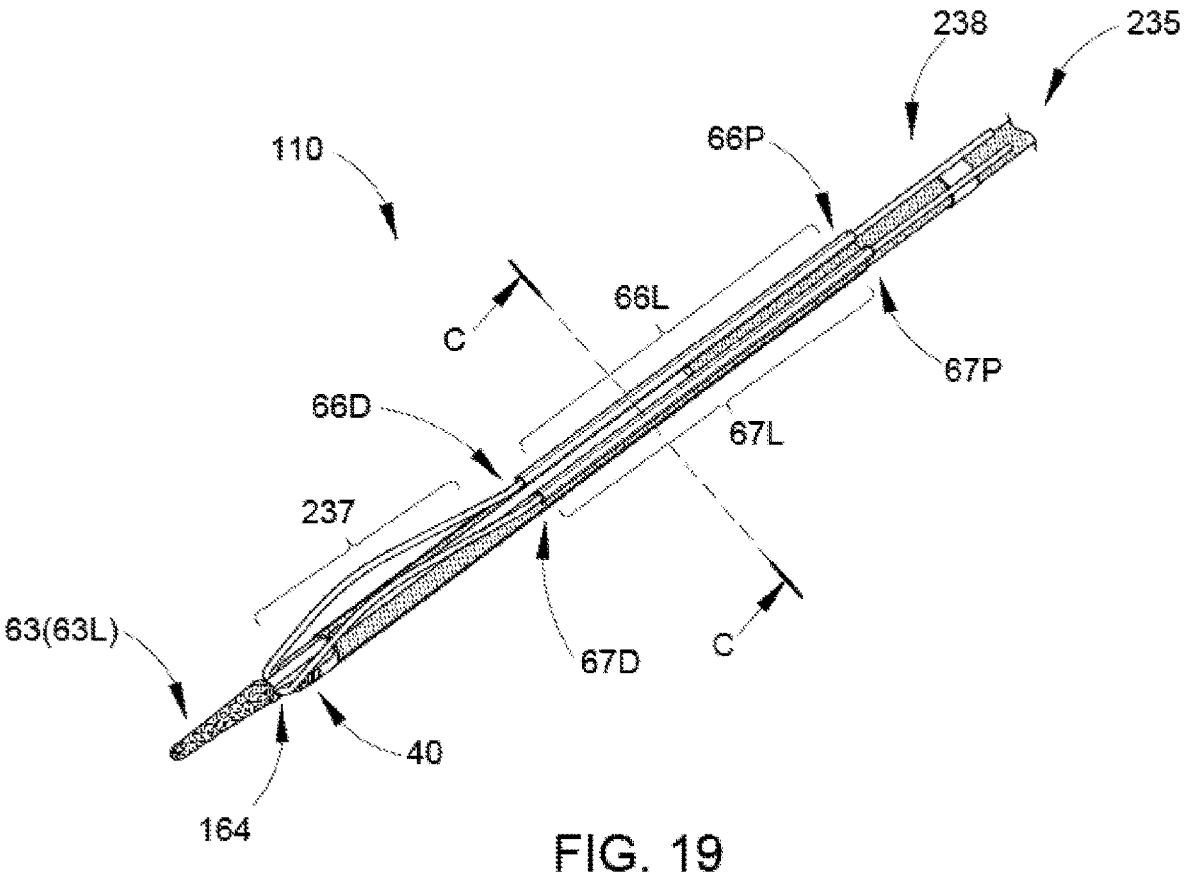
FIGS. 19-20 depict a distal portion of a catheter and a pusher according to a third embodiment.
Figure 20:
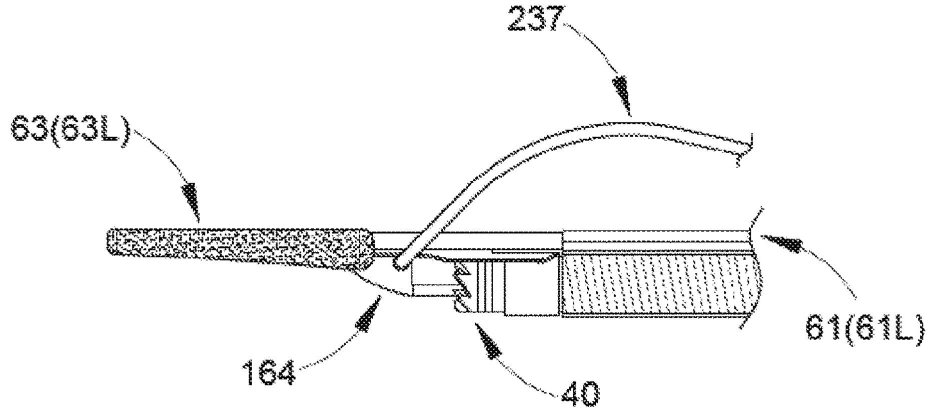

FIGS. 19-20 depict a distal portion of a catheter 110 and a pusher 235 according to a third embodiment. In this embodiment, the catheter 110 includes the pusher 235 that is attached to the distal end thereof. During operation, the operator does not need to insert the pusher 235 and the catheter 110 separately. Similar to the pusher 35 or 135 described above, the pusher 235 includes a bent portion 237 and a straight portion 238. For example, the pusher 235 is formed of an elastic wire, e.g., a nitinol wire, having a diameter of 0.2 mm to 0.5 mm. FIG. 20 is an enlarged view of the bent portion 237 and the straight portion 238 of the pusher 235.

Figure 21:
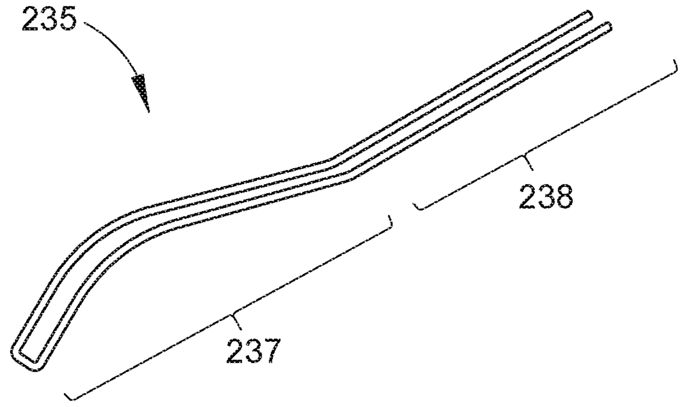
FIG. 21 depicts the pusher according to the third embodiment prior to attachment to the catheter.
Figure 22:
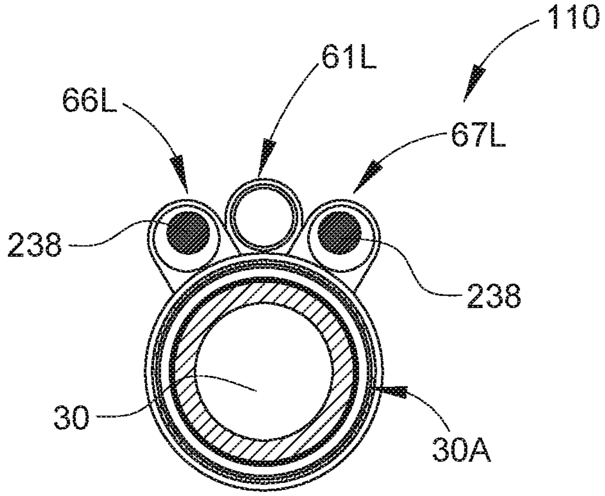
FIG. 22 depicts the catheter to be used with the pusher according to the third embodiment.

FIG. 21 depicts the pusher 235 according to the third embodiment prior to attachment to the catheter 110. The distal end of the bent portion 237 fits in a recess or an opening formed in a metal member 164 and is rotatably held therein by the guide wire tube 61. The straight portion 238 is formed of two wires, which pass through the corresponding lumens 66L and 67L and run along the outer tube 30A toward the proximal side. FIG. 22 is a cross-section of the catheter 110 taken along line C-C shown in FIG. 19. The lumens 66L and 67L through which the wires of the straight portion 238 pass are disposed adjacent to the guide wire lumen 61L in this example, but those lumens 66L and 67L can be disposed at any locations along the outer tube 30A.

Figure 23:
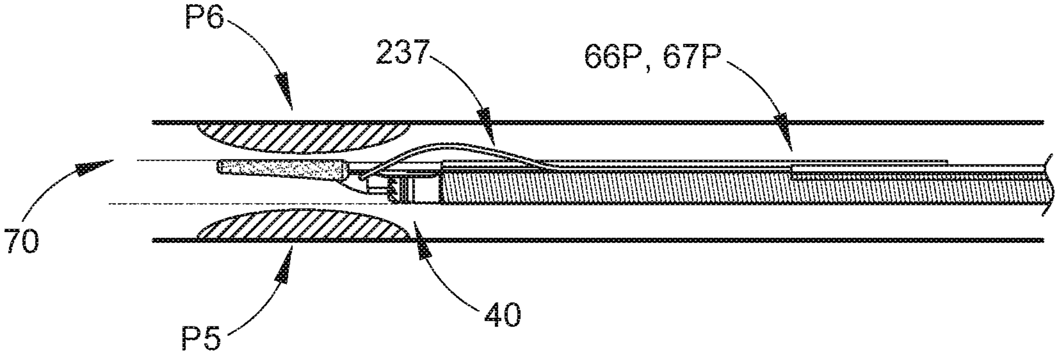
FIGS. 23-24 depict the catheter of FIGS. 19-20 approaching an object to be removed in a body lumen.
Figure 24:
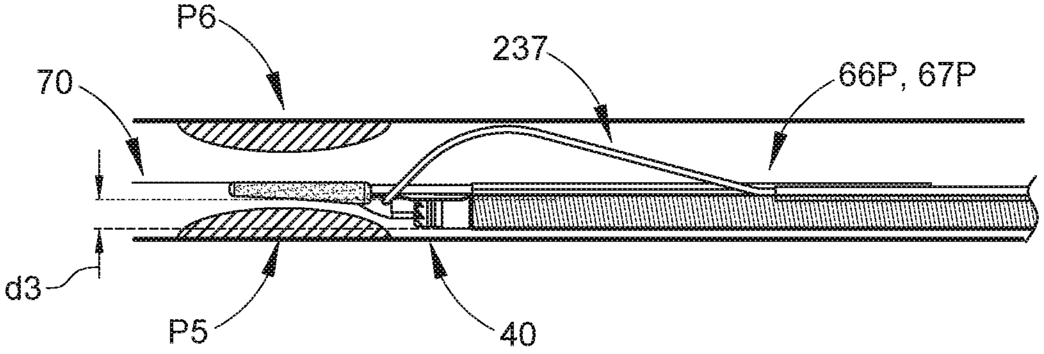

FIGS. 23-24 depict the catheter of FIGS. 19-20 approaching target objects formed on a body lumen. As explained above, during operation, the guide wire 70 is inserted into a body lumen first. Here, there is no need to insert the pusher 235 separately because it is attached to the catheter 110. As shown in FIG. 23, the operator moves the catheter 110 along the guide wire 70 to reach positions P5 and P6 at which the target objects are formed. In that state, outside the body lumen, the operator moves the straight portion 238 of the pusher 235 forward while maintaining the position of the drive shaft 30 or the outer tube 30A, thereby increasing the curvature of the bend portion 237 inside the body lumen as shown in FIG. 24. By this operation, the cutting portion 40 is moved toward the object at position P5 (i.e., downward) by d3 because the bent portion 237 contacts and pushes the body lumen and/or the object near position P6. Similarly, the object on the opposite side at position P6 can be removed by changing the orientation of the catheter 110. Thus, the catheter 110 can achieve a larger cutting diameter, which is increased by d3*2 compared to a conventional catheter without the pusher 237.

Figure 25:
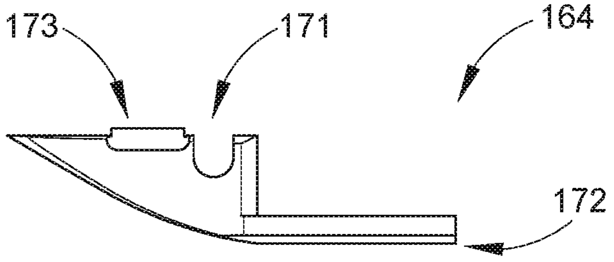
FIGS. 25-26 depict a metal member used for the catheter of FIGS. 19-20.
Figure 26:
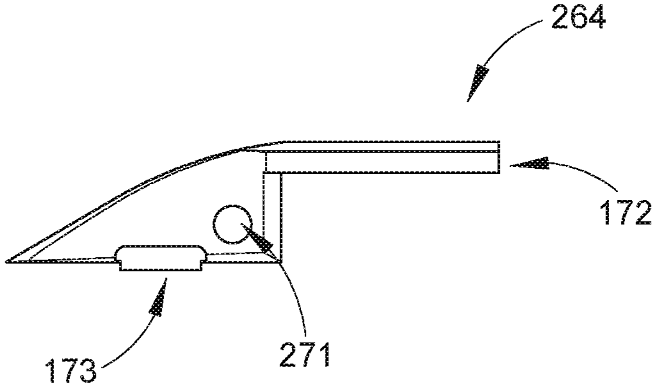

FIGS. 25-26 each depict a metal member to be connected to the pusher 235. FIG. 25 depicts the metal member 164 shown in FIG. 20, and FIG. 26 depicts a metal member 264 which has a different configuration. Each of the metal member 164 and the metal member 264 is a modified version of the metal member 64.

With reference to FIG. 25, the metal member 164 includes a recess 171, a protector 172, and a bonding surface 173. The distal end of the bent portion 237 of the pusher 235 fits in the recess 171 in a rotatable manner. The protector 172 is partially inserted into the cutting member 40 as shown in FIG. 4, and stops the cutting member 40 from proceeding further when the catheter 110 is unintentionally guided toward a body lumen. The bonding surface 173 is bonded to the guide wire tube 61.

As shown in FIG. 26, the metal member 264 may have a hole through which the distal end of the bent portion 237 can pass. With this configuration, the pusher 235 can be secured to the metal member 264 more strongly without the need for covering the recess 171 as shown in FIG. 25. Since the pusher 235 is secured to the metal member 164 or 264, when a force to push the bent portion 237 toward the outer tube 30A is applied, the offset created by the bent portion 237 can collapse and the pusher 235 extends straight along the outer tube 30A.

Figure 27:
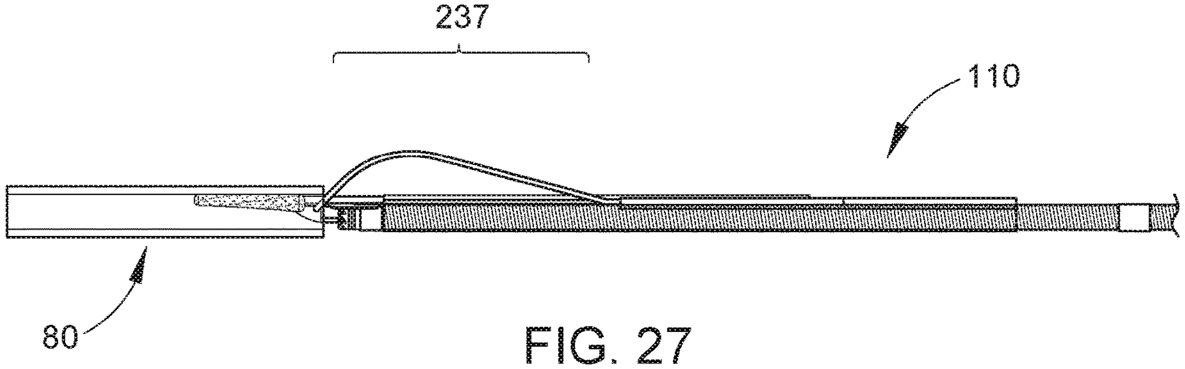
FIGS. 27-28 depict the catheter of FIGS. 19-20 passing through an introducer sheath.
Figure 28:
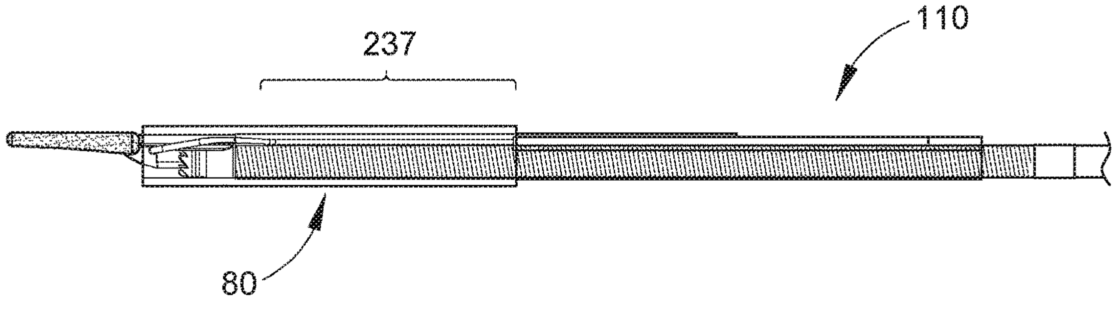

FIGS. 27-28 depict the catheter 110 with the pusher 235, which enters an introducer sheath 80 having a certain diameter that is slightly larger than the outer tube 30A. When the catheter 110 passes through the sheath 80, the bent portion 237 of the pusher 235 is pushed toward the outer tube 30A, thereby becoming straight because of its elastic feature. Thus, the catheter 110 is not prevented from entering into the sheath 80 even with the offset created by the bent portion 237.

Figure 29:
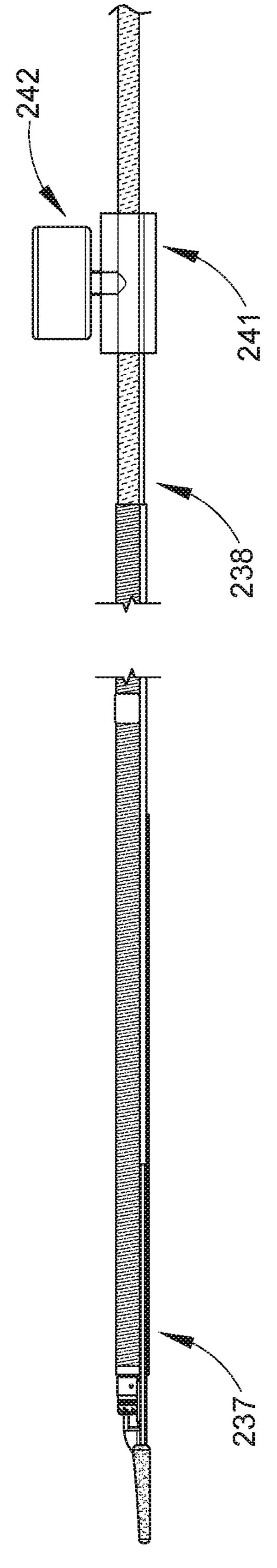
FIGS. 29-30 depict the catheter of FIGS. 19-20 having a slider at a proximal portion thereof.
Figure 30:
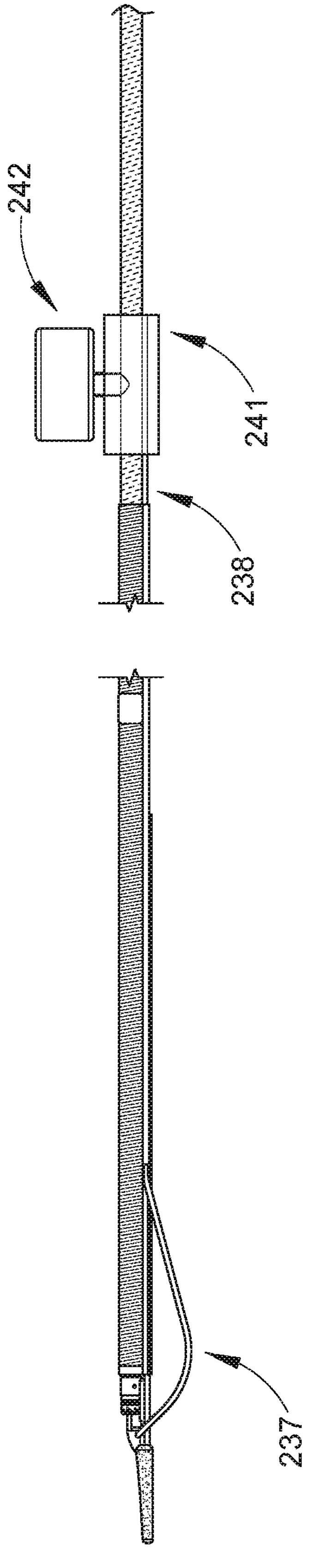

In one embodiment, the catheter 110 has a sliding and locking mechanism for adjusting the curvature of the bent portion 237, at the proximal portion of the catheter 110. As shown in FIGS. 29-30, the catheter 110 includes a slider 241 connected to the proximal end of the pusher 235 (i.e., the straight portion 238) and capable of sliding along the outer tube 30A outside a body lumen during an operation. The catheter 110 further includes a finger screw 242 for locking the position of the slider 241. With this configuration, the operator can adjust the curvature of the bent portion 237 by changing the position of the slider 241.

Figure 31:
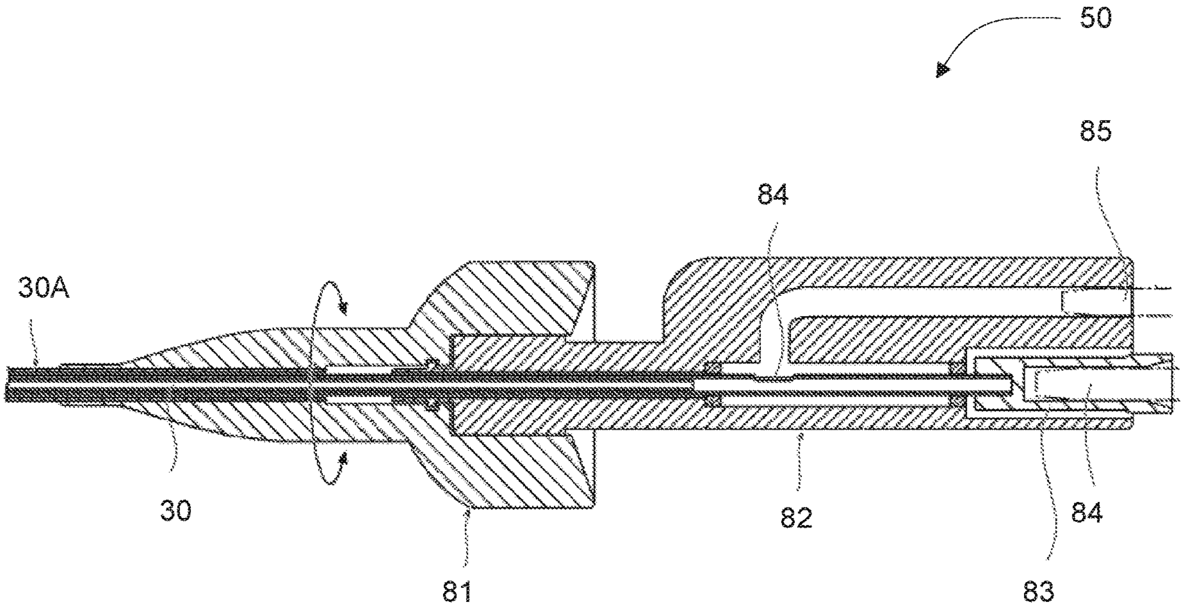
FIG. 31 depicts a proximal portion of a catheter and a hub.

FIG. 31 depicts a proximal portion of the catheter 10 or 110 and the hub 50 into which the drive shaft 30 is inserted. The hub 50 includes a rotatable knob 81 and a connector 82 connectable to the handle 20. The knob 81 is connected to the outer tube 30A and rotatable by an operator so as to adjust an orientation and/or location of the drive shaft 30 and the cutting member 40 inside a body lumen during an operation. The knob 81 allows the outer tube 30A to rotate independently of the drive shaft 30 and the connector 82.

The drive shaft 30 is, directly or indirectly via one or more other shafts, connected to a coupler 83 with a recess 84 that can engage with a drive shaft (not shown) connected to the torque generating element inside the handle 20. Further, the aspiration lumen of the drive shaft 30 communicates with an aspiration port 85 via an opening 84 inside the connector 82. When the catheter 10 or 110 is connected to the handle 20 via the connecter 82, the generated torque is transmitted to the drive shaft 30 via the coupler 83 while the object that has entered the aspiration lumen of the drive shaft 30 is discharged from the aspiration port 85 via the opening 84.

Figure 32:
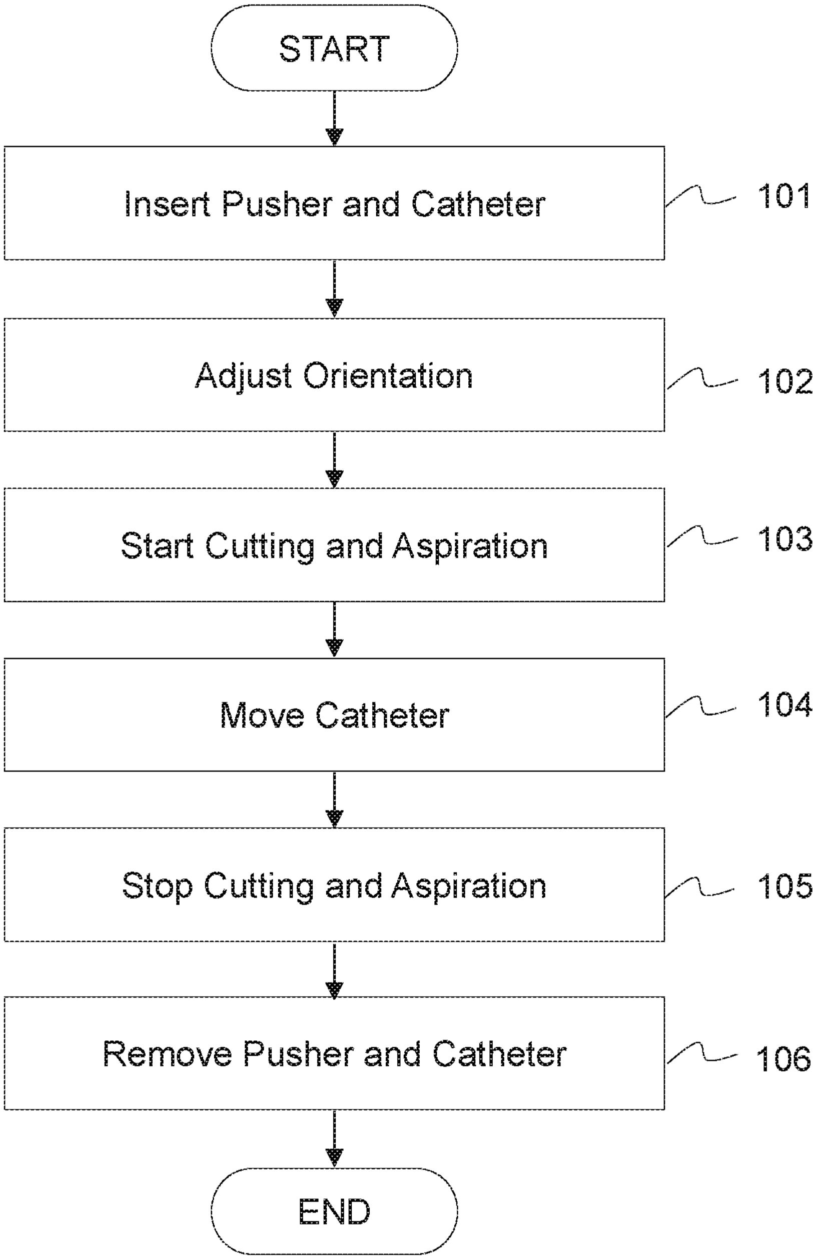
FIG. 32 depicts a flowchart of a method for removing an object in a body lumen.

FIG. 32 depicts a flowchart of a method for removing an object in a body lumen using the medical device 1 or the catheter 10 or 110 described above. At the beginning of a medical operation, the operator connects the catheter 10 or 110 to the handle 20 via the hub 50 and inserts a guide wire 70 into the body lumen from its distal end using an introducer sheath 80 so that the guide wire 70 passes near a target location where the object is formed. After those steps, the operator inserts the pusher 35 or 135 and the catheter 10 separately, or inserts the catheter 110 together with the pusher 235, along the guide wire 70 through the sheath 80 (Step 101).

Once the distal end of the catheter 10 or 110 has reached the target location, the operator rotates the knob 81 to adjust the orientation and/or location of the catheter 10 or 110 inside the body lumen so that the cutting member 40 is directed toward the object by the curvature of the drive shaft 30 (Step 102). The operator then turns on the aspiration and torque generating mechanisms of the handle 20 to start cutting and aspirating the object (Step 103), and moves the catheter 10 forward along the guide wire 70 until the target object is removed and aspirated (Step 104).

Once the target object has been removed, the operator turns off the aspiration and torque generating mechanisms (Step 105), and removes the catheter 10 or 110 and the pusher 35, 135, or 235 from the body lumen (Step 106). The guide wire 70 and introducer sheath 80 are removed thereafter.

The order of one or more of the steps shown in FIG. 32 can be modified. For example, the aspiration and torque generating mechanisms can be turned on at any time after the catheter 10 or 110 has been inserted into the body lumen. Additionally, one or more of the steps can be repeated if necessary. For example, the orientation of the catheter 10 or 110 can be adjusted at any time during the operation to remove the object.

What is claimed is:

1. A catheter for removing an object in a body lumen, comprising:

an outer tube;

a rotatable drive shaft surrounded by the outer tube;

a cutting member connected to a distal end of the drive shaft to be rotated by the drive shaft with respect to a rotation axis and by which the object is cut;

a guide wire tube attached to a distal end of the outer tube and having a plurality of lumens extending parallel to the rotation axis, the plurality of lumens including a first lumen through which a guide wire can pass and one or more second lumens;

a metal member attached to the guide wire tube, a part of the metal member being surrounded by the cutting member;

a distal tip attached to a distal end of the guide wire tube and having a third lumen extending parallel to the rotation axis and communicating with the first lumen; and a pusher at least partially extending along the drive shaft, connectable to either the distal tip or the metal member, and including one or more first wires that can pass through the one or more second lumens, wherein the pusher causes the cutting member to move toward a first inner surface of the body lumen when the pusher contacts a second inner surface that is on an opposite side of the body lumen with respect to the first inner surface.

2. The catheter according to claim 1, wherein the pusher further includes a plurality of second wires, each of which is at least partially bent to protrude in a direction away from the cutting member.

3. The catheter according to claim 2, wherein a distal end of the pusher is connected to the metal member.

4. The catheter according to claim 3, wherein the metal member has a recess with which the distal end of the pusher engages and a surface contacting the guide wire tube.

5. The catheter according to claim 3, wherein the metal member has a hole through which the distal end of the pusher passes.

6. The catheter according to claim 3, wherein the pusher is formed of an elastic wire.

7. The catheter according to claim 6, wherein the pusher is made of nitinol.

8. The catheter according to claim 6, wherein the elastic wire has a diameter of 0.2 mm to 0.5 mm.

9. The catheter according to claim 6, wherein the second wires become straight when pushed toward the rotation axis.

10. The catheter according to claim 2, further comprising:
a slider connected to a proximal end of the first wires of the pusher and slidable along the outer tube.

11. The catheter according to claim 10, further comprising:
a screw by which a position of the slider can be locked.

12. The catheter according to claim 2, wherein the pusher further includes a head portion connected to the second wires and connectable to the distal tip.

13. The catheter according to claim 12, wherein the head portion has a fourth lumen through which the guide wire can pass.

14. The catheter according to claim 12, wherein the guide wire tube has a single second lumen, and the pusher has a single second wire that can pass through the single second lumen.

15. The catheter according to claim 1, wherein the guide wire tube has two second lumens between which the first lumen is formed, and the pusher has two first wires that can pass through the corresponding two second lumens.

16. A medical device for removing an object in a body lumen, comprising:
a handle including a motor configured to generate rotation torque; and
a catheter connectable to the handle and including:
an outer tube,
a drive shaft surrounded by the outer tube and rotatable by the generated rotation torque,
a cutting member connected to a distal end of the drive shaft to be rotated by the drive shaft with respect to a rotation axis and by which the object is cut,
a guide wire tube attached to a distal end of the outer tube and having a plurality of lumens extending parallel to the rotation axis, the plurality of lumens including a first lumen through which a guide wire can pass and one or more second lumens,
a metal member attached to the guide wire tube, a part of the metal member being surrounded by the cutting member,
a distal tip attached to a distal end of the guide wire tube and having a third lumen extending parallel to the rotation axis and communicating with the first lumen, and
a pusher at least partially extending along the drive shaft, connectable to either the distal tip or the metal member, and including one or more first wires that can pass through the one or more second lumens, wherein
the pusher causes the cutting member to move toward a first inner surface of the body lumen when the pusher contacts a second inner surface of the body lumen that is on an opposite side of the body lumen with respect to the first inner surface.

17. The medical device according to claim 16, wherein the catheter is connectable to the handle via a hub, and the hub includes a knob connected to and rotatable with the outer tube.

18. The medical device according to claim 16, wherein a distal end of the pusher is connected to the metal member.

19. A method for removing an object in a body lumen using a catheter that includes:
an outer tube,
a rotatable drive shaft surrounded by the outer tube,
a cutting member connected to a distal end of the drive shaft to be rotated by the drive shaft with respect to a rotation axis and by which the object is cut,
a guide wire tube attached to a distal end of the outer tube and having a plurality of lumens extending parallel to the rotation axis, the plurality of lumens including a first lumen through which a guide wire can pass and one or more second lumens,
a metal member attached to the guide wire tube, a part of the metal member being surrounded by the cutting member,
a distal tip attached to a distal end of the guide wire tube and having a third lumen extending parallel to the rotation axis and communicating with the first lumen, and
a pusher at least partially extending along the drive shaft, connectable to either the distal tip or the metal member, and including one or more first wires that can pass through the one or more second lumens, the method comprising:
inserting the catheter into the body lumen;
moving either the drive shaft or the pusher with respect to the other along the rotation axis such that the pusher contacts a first inner surface of the body lumen;
positioning the cutting member to an object on a second inner surface that is on an opposite side of the body lumen with respect to the first inner surface and removing the object; and
removing the catheter from the body lumen.

20. The method according to claim 19, further comprising:
inserting an introducer sheath before inserting the catheter, wherein
the pusher is formed of a partially bent elastic wire, and
inserting the catheter includes inserting the catheter into the sheath such that the pusher becomes straight when passing through a lumen of the sheath.

21. A catheter for removing an object in a body lumen, comprising:
an outer tube;
a rotatable drive shaft surrounded by the outer tube;
a cutting member connected to a distal end of the drive shaft to be rotated by the drive shaft with respect to a rotation axis and by which the object is cut;
a guide wire tube attached to a distal end of the outer tube and having a plurality of lumens extending parallel to the rotation axis, the plurality of lumens including a first lumen through which a guide wire can pass and one or more second lumens;
a distal tip attached to a distal end of the guide wire tube and having a third lumen extending parallel to the rotation axis and communicating with the first lumen; and
a pusher at least partially extending along the drive shaft, connectable to the distal tip, and including one or more first wires that can pass through the one or more second lumens, wherein the pusher causes the cutting member to move toward a first inner surface of the body lumen when the pusher contacts a second inner surface that is on an opposite side of the body lumen with respect to the first inner surface.

* * * * *